(12) United States Patent  
Hariyama et al.

(10) Patent No.: US 8,018,585 B2  
(45) Date of Patent: Sep. 13, 2011

(54) SURFACE DEFECT INSPECTING APPARATUS WITH DEFECT DETECTION OPTICAL SYSTEM AND DEFECT-DETECTED IMAGE PROCESSING

(75) Inventors: Tatsuo Hariyama, Fujisawa (JP); Minoru Yoshida, Yokohama (JP); Shigeru Serikawa, Chigasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 6 days.

(21) Appl. No.: 12/327,849

(22) Filed: Dec. 4, 2008

(65) Prior Publication Data

US 2009/0237669 A1    Sep. 24, 2009

(30) Foreign Application Priority Data

Dec. 7, 2007   (JP) ................................. 2007-316524

(51) Int. Cl.  
*G01N 21/00*   (2006.01)

(52) U.S. Cl. ................... 356/237.2; 356/239.3; 356/448; 356/445

(58) Field of Classification Search .... 356/237.1–237.6, 356/442, 445, 239.7, 239.8, 238.3, 448  
See application file for complete search history.

(56) References Cited

U.S. PATENT DOCUMENTS

| | | | | |
|---|---|---|---|---|
| 5,677,762 A | * | 10/1997 | Ortyn et al. | 356/443 |
| 7,465,935 B2 | * | 12/2008 | Urano et al. | 250/372 |
| 7,505,125 B2 | * | 3/2009 | Andrews et al. | 356/237.2 |
| 7,528,944 B2 | * | 5/2009 | Chen et al. | 356/237.6 |
| 2009/0059216 A1 | * | 3/2009 | Shibata et al. | 356/237.4 |

FOREIGN PATENT DOCUMENTS

| | | |
|---|---|---|
| JP | 2001-174415 | 6/2001 |
| JP | 2003-035678 | 2/2003 |

* cited by examiner

*Primary Examiner* — Gregory J Toatley  
*Assistant Examiner* — Iyabo S Alli  
(74) *Attorney, Agent, or Firm* — Antonelli, Terry, Stout & Kraus, LLP.

(57) ABSTRACT

There is provided a defect inspecting apparatus, which includes an irradiating optical system of irradiating a light beam on a surface of a face plate of a disk mounted on a stage to scan the surface of the face plate, a light-receiving optical system of receiving specular reflection light that has transmitted a shading filter with a shading difference that changes an amount of the specular reflection light from the face plate resulting from the light beam irradiated on the disk, and a processing unit of identifying defects on the surface of the face plate from the change in amount of the specular reflection light that has transmitted a filter, so that a size and a height of the defect can be measured with high accuracy when irregular defects are determined, which is not easily achieved by a conventional lens effect.

15 Claims, 16 Drawing Sheets

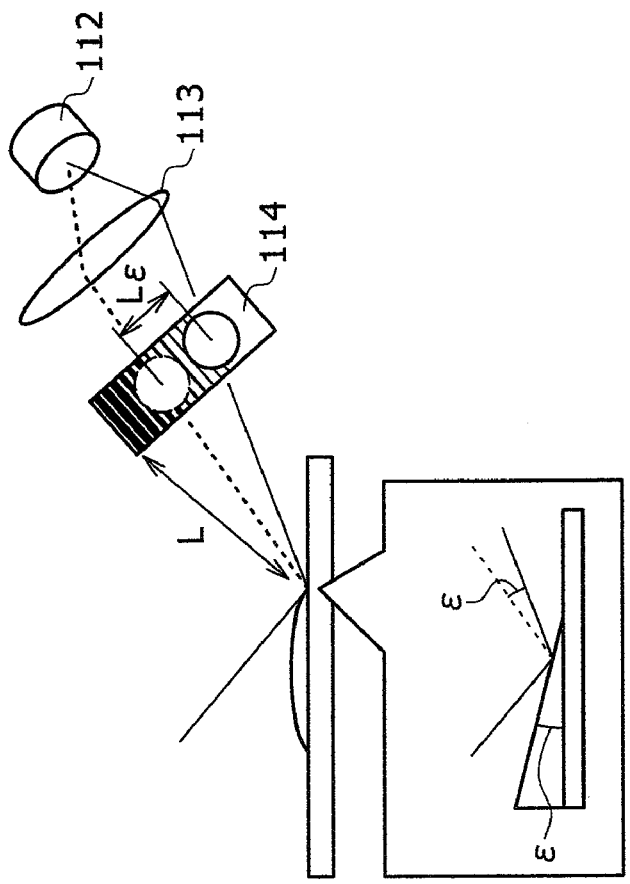
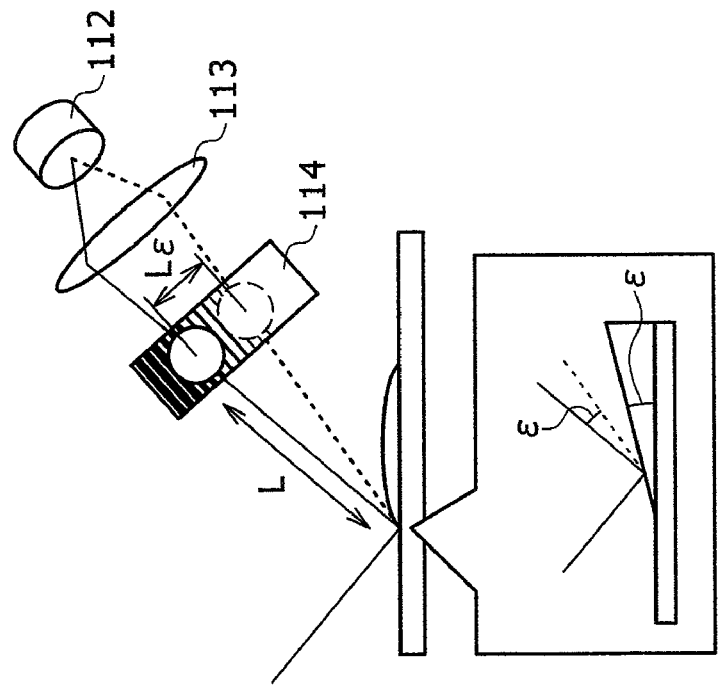
FIG. 3A
FIG. 3B

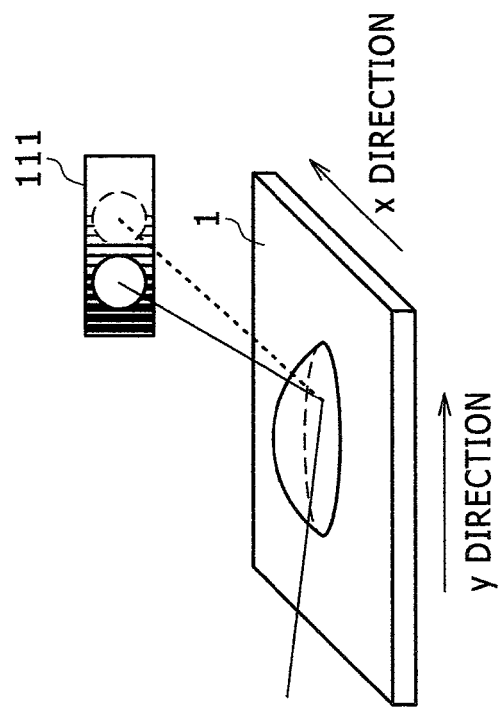
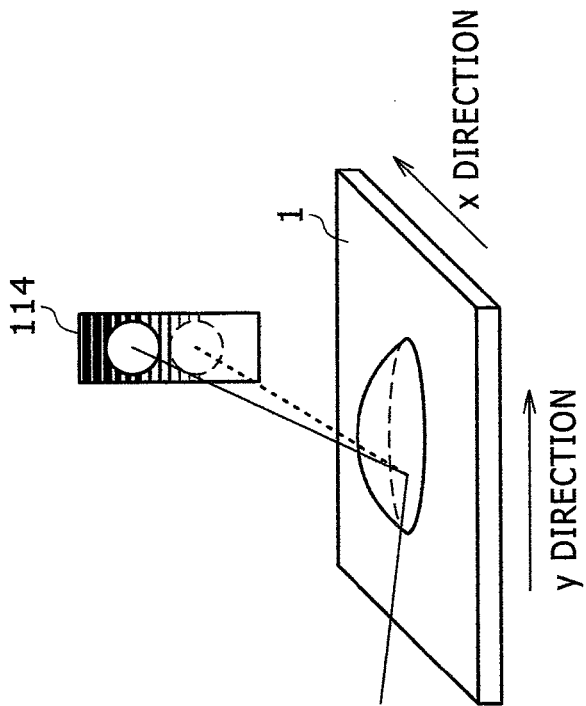
FIG. 5A
FIG. 5B

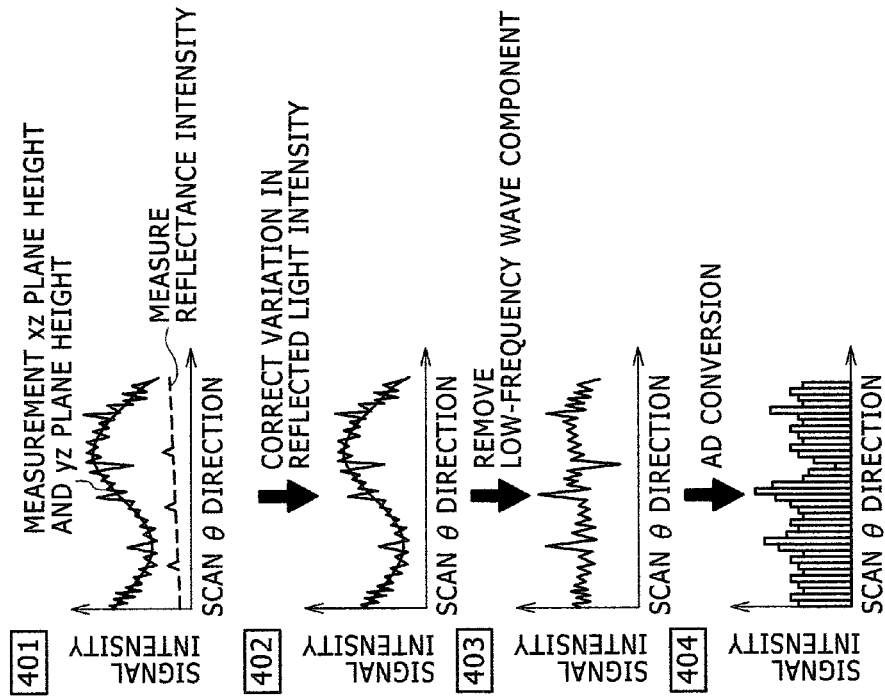
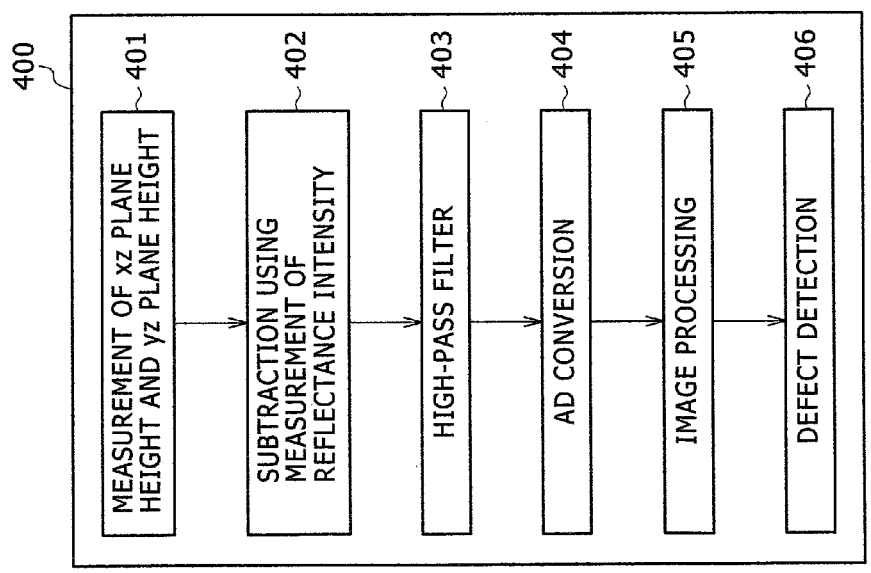

FIG.7A
LINE-SHAPED DISTRIBUTION DEFECT
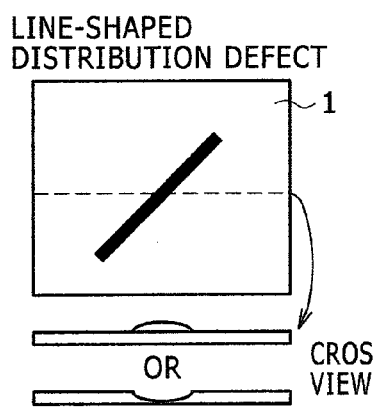
FIG.7B
ARC-SHAPED DISTRIBUTION DEFECT
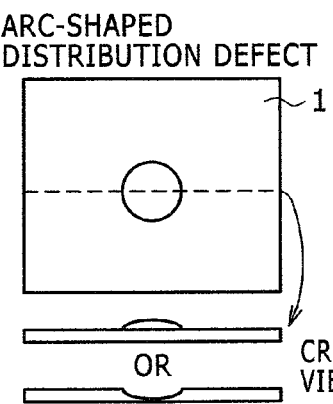
FEATURE ON IMAGE
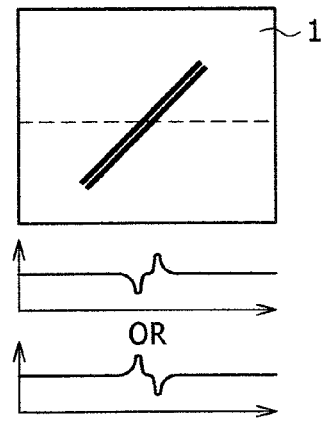
FEATURE ON IMAGE
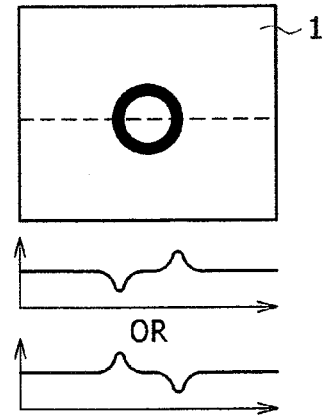

FIG.8A
FIG.8B
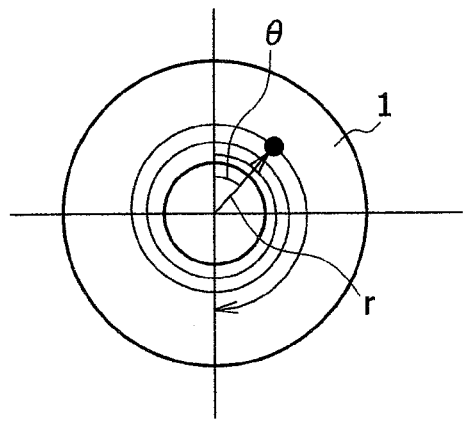
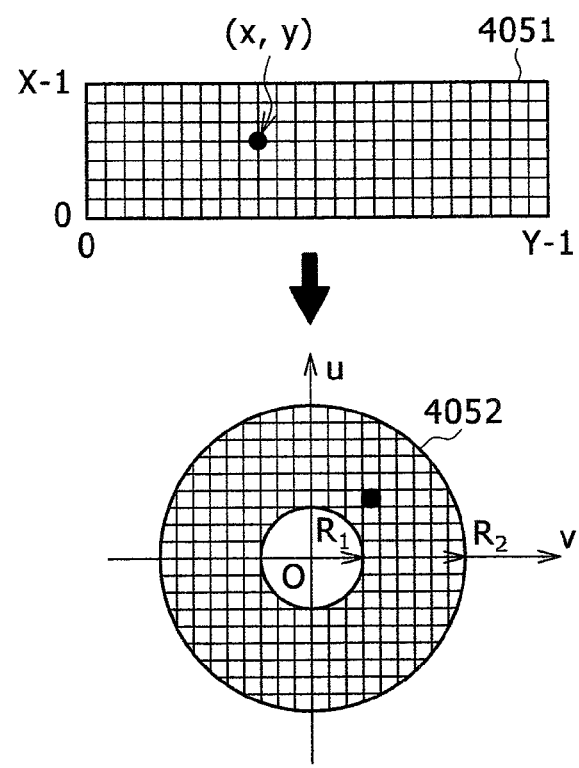

FIG.10A  FIG.10C
 FIG.10B   FIG.10D
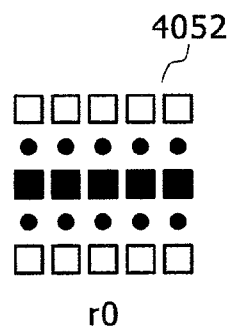
r0
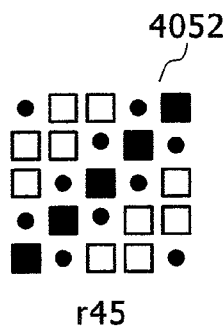
r45
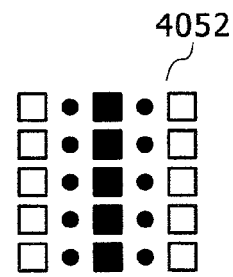
r90
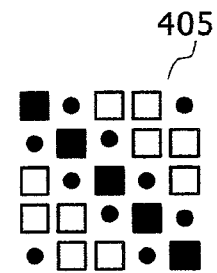
r135
FIG.11
| | | | | 4053 | | |
|---|---|---|---|---|---|---|
| $W_3$ | $W_3$ | $W_3$ | $W_3$ | $W_3$ | $W_3$ | $W_3$ |
| $W_3$ | $W_2$ | $W_2$ | $W_2$ | $W_2$ | $W_2$ | $W_3$ |
| $W_3$ | $W_2$ | $W_1$ | $W_1$ | $W_1$ | $W_2$ | $W_3$ |
| $W_3$ | $W_2$ | $W_1$ | ■ | $W_1$ | $W_2$ | $W_3$ |
| $W_3$ | $W_2$ | $W_1$ | $W_1$ | $W_1$ | $W_2$ | $W_3$ |
| $W_3$ | $W_2$ | $W_2$ | $W_2$ | $W_2$ | $W_2$ | $W_3$ |
| $W_3$ | $W_3$ | $W_3$ | $W_3$ | $W_3$ | $W_3$ | $W_3$ |

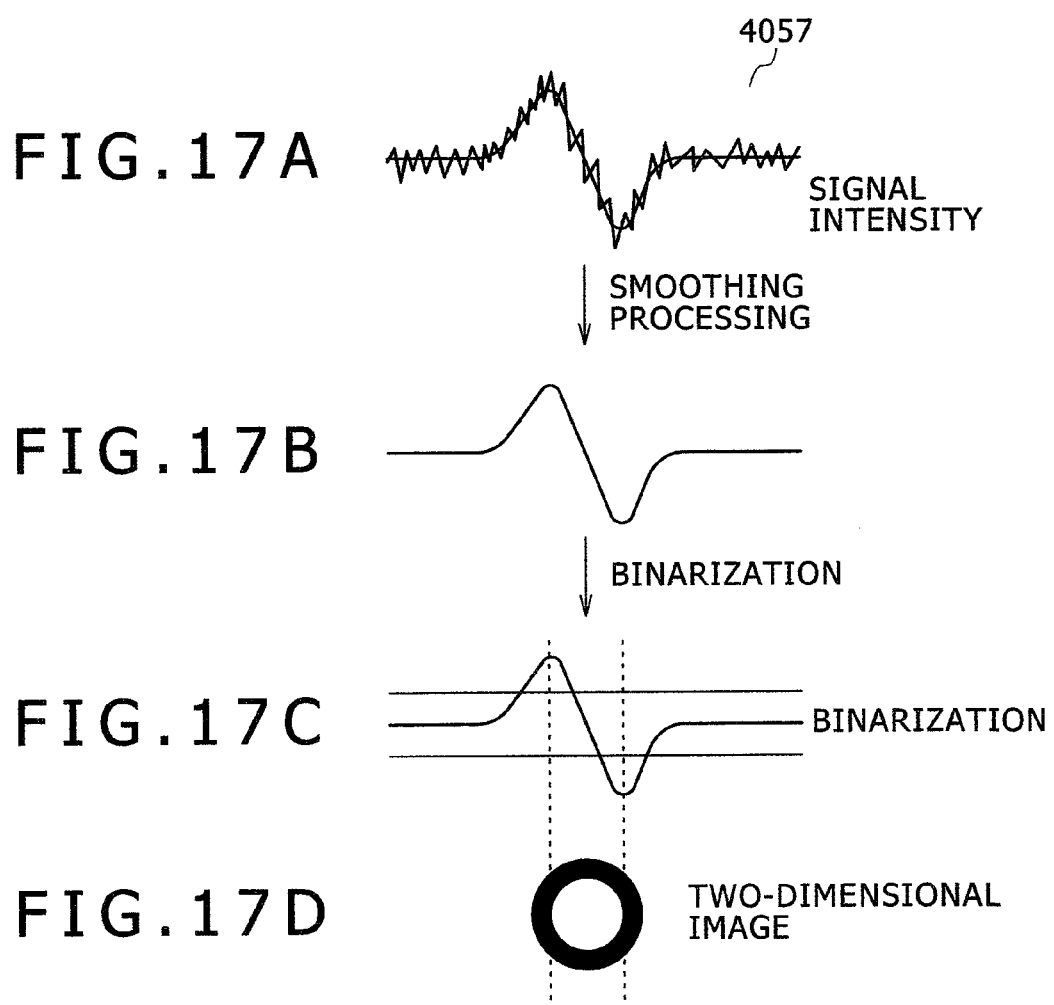

FIG.20A    FIG.20B
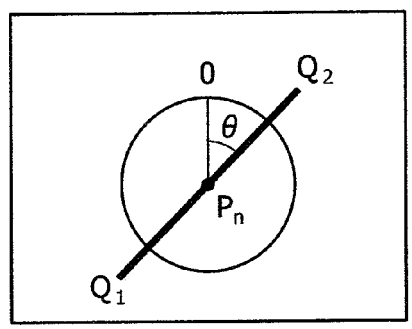 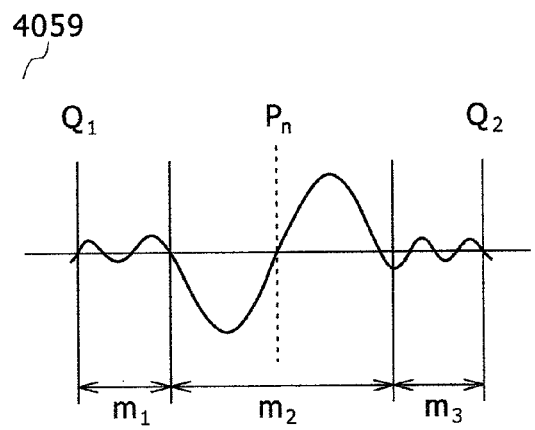
FIG.21
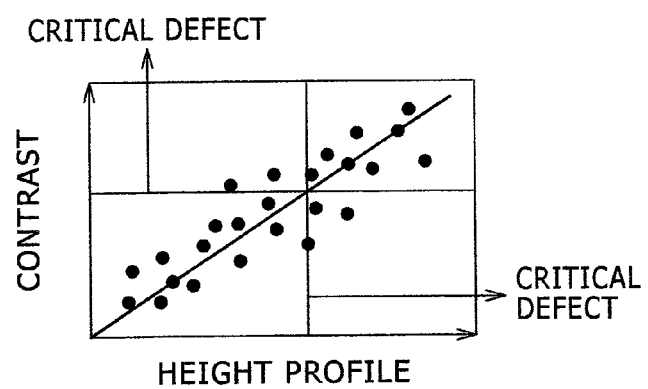

SURFACE DEFECT INSPECTING APPARATUS WITH DEFECT DETECTION OPTICAL SYSTEM AND DEFECT-DETECTED IMAGE PROCESSING

CLAIM OF PRIORITY

The present application claims priority from Japanese Patent Application JP 2007-316524 filed on Dec. 7, 2007, the content of which is hereby incorporated by reference into this application.

FIELD OF THE INVENTION

The present invention relates to a surface defect inspecting apparatus, and in particular, to a surface defect inspecting apparatus of a face plate such as a magnetic disk or its aluminum plate (i.e., an aluminum substrate) or a glass plate (i.e., a glass substrate), which can detect with high accuracy the size of a concave defect or a convex defect on the surface of the face plate and can further detect with high accuracy the size and the depth or the size and the height, of an irregular defect on the surface of the face plate.

DESCRIPTION OF THE RELATED ART

A technique of detecting with high accuracy the concave defects and the convex defect is disclosed in JP-A-Hei13 (2001)-174415, wherein a light receiver has a sensor array composed of plural Avalanche Photo Diode (APD) elements, stripe patterns having a zigzag shape are arranged to correspond to the elements in front of the light receiver, and the recess and convex defects can be detected by the difference between amounts of light received from the adjacent light-receiving elements. Alternatively, a technique of not using the stripe patterns having the zigzag shape is also disclosed in JP-A-Hei13 (2001)-174415.

In the meantime, a technique of detecting a concave defect or a convex defect by providing a light-receiving system is disclosed in JP-A-Hei15 (2003)-35678, wherein the light-receiving system includes n pieces of arranged light-receiving elements, and images formed along a direction at right angles to a main scanning direction correspond to the arrangement direction of the light-receiving elements. Such a concave defect or a convex defect causes an upper limit peak and a lower limit peak to be generated in detection signals of the respective light-receiving elements in the arrangement direction of the n light-receiving elements due to lens effect of the respective defects.

According to the techniques disclosed in JP-A-Hei13 (2001)-174415, to obtain detection signals having different waveforms from the recess and convex defects, it is required to arrange the sensor array composed of the APD elements in two parallel lines. Accordingly, discrimination between the recess and convex defects can be done on the basis that which one of the two lines of the light-receiving elements first receives light to generate the detection signal. In order to detect various defects with high accuracy, the number of the elements in the light receiver ranges from more than 10 and less than 20 to several tens of elements. This is why plural circuits receiving signals from adjacent elements in the width direction of the adjacent elements are disadvantageously required in the related art. Further, according to the technique disclosed in JP-A-Hei15 (2003)-35678, irregular defects are determined by the lens effect, so that the accuracy is not good in terms of exact size and height of the defect.

SUMMARY OF THE INVENTION

The present invention is directed to a surface defect inspecting apparatus, which can employ a small number of detectors and circuits to detect with high accuracy the size and the height of a concave defect or a convex defect on the surface of a face plate.

One aspect of the present invention is to provide a surface defect inspecting apparatus with a defect detection optical system and defect-detected image processing, including: an irradiating optical system of irradiating a light beam on a surface of a face plate of a disk mounted on a stage to scan the surface of the face plate; a light-receiving optical system including a shading filter having a shading difference causing an amount of specular reflection light from the face plate resulting from the light beam irradiated on the disk to be changed and receiving the specular reflection light that has transmitted the shading filter; and processing means for identifying a defect on the surface of the face plate from the change in amount of the specular reflection light that has transmitted the shading filter. Another aspect of the present invention is to provide a surface defect inspecting apparatus, which carries out a processing method according to kinds of defect from defect data obtained from the inspected surface of the face plate, so that defects having features on the surface of the face plate, e.g., stripe defects or circular arc defects can be detected and sizes or heights thereof can be measured with high accuracy.

The present invention determines recess and convex defects by arranging the filter having the shading difference mentioned above in front of the light-receiving elements. The shading filter has the shading difference ranging from a region with a transmittance of 0% to a region with a transmittance of 100% and is set to allow the specular reflection light of the light beam that has irradiated the place where no defects are present on the surface of the face plate to transmit the position of transmittance of 50%, that is, the central position of the filter. When the concave defect or the convex defect is present, the region where the specular reflection light from a lateral inclined portion of the concave defect or the convex defect transmits the filter is shifted to any one of the region having a high transmittance and the region having a low transmittance. After the light transmits the filter with this arrangement, the amount of light received by the light-receiving elements is changed, so that the defects can be detected from the change.

When the irregular defects on the surface of the face plate are read out from the change in amount of light received by the light receiver through the filter having the shading difference, portions (spots and so forth) having different reflectance on the surface of the face plate may be detected as irregular defects. To deal with this possible problem, the change in reflectance on the surface is measured by separately arranging a light-receiving system using direct light-receiving elements apart from the light-receiving elements described above without having the specular reflection light from the surface of the face plate transmit the shading filter. By subtracting the amount of light used for measuring the change in specular reflectance from the amount of light received by the light-receiving elements through the shading filter having the shading difference, it is possible to accurately detect the irregular defects without being affected by the change in reflectance on the surface of the face plate.

In this case, the generated defect detection signal deviated from the position having the transmittance of 50% of the shading filter due to the inclination of the irregular defect on the surface typically causes two peaks such as positive and negative peaks to be generated on each of the recess and convex defects. With this arrangement, the size of the defect can be detected by the distance between these peaks. In addition, the reason why the concave defect or the convex defect causes two peaks to be generated lies in that any of both defects typically has a pair of lateral inclined portions in the scanning direction of R and θ. When the irradiation position (i.e., the coordinate position) where the positive and negative peaks of the defect detection signal are generated is detected, the distance between the peaks can be obtained, and the width or the area depending on the size of the defect can be easily calculated from the relationship between the distance and the irradiation position. The present invention can easily determine the continuity of the detected defects from the relationship between the coordinate position of the detected defects and the distance between the peaks with respect to the detected defects. With this determination, the width or the area can be easily calculated even with respect to some deformed defects of the concave defect or the convex defect. The present invention can take an average of absolute values of both positive and negative peaks to detect with high accuracy the depth of the concave defect or the height of the convex defect. As a result, the present invention can detect with high accuracy the size of the irregular defect on the surface of the face plate to implement the surface defect inspecting apparatus facilitating defect classification.

An exemplary summary of the present invention that have the features described above or that will be evident from embodiments to be described later is as follows.

(1) One aspect of the present invention is to provide a defect inspecting apparatus, which includes: an irradiating optical system of irradiating a light beam on a surface of a disk; a first light-receiving optical system of having specular reflection light from the disk resulting from the light beam irradiated on the disk transmit a first filter having a shading difference to receive the specular reflection light; and a signal processing means for detecting defects on the disk based on an amount of light obtained by the first light-receiving optical system.

(2) In the defect inspecting apparatus according to the one aspect of the present invention, the apparatus further includes a second light-receiving optical system of having the specular reflection light from the disk resulting from the light beam irradiated on the disk transmit a second filter and receiving the specular reflection light, wherein the first filter is a filter having a shading difference in a direction substantially orthogonal to the specular reflection light in an xz plane, and the second filter is a filter having a shading difference in a direction substantially orthogonal to the specular reflection light in a yz plane.

(3) In the defect inspecting apparatus according to the one aspect of the present invention, the defect inspecting apparatus further includes a third light-receiving optical system that receives specular reflection light from the disk resulting from the light beam irradiated on the disk, wherein the signal processing means subtracts an amount of light obtained by the third light-receiving optical system from the amount of light obtained by the third light-receiving optical system to detect the defects on the disk.

(4) Another aspect of the present invention is to provide a method of analyzing defect data, which includes carrying out processing according to kinds of defects based on defect data obtained from an inspected surface of a disk to detect defects having features on the surface, and setting as a threshold a predetermined width or a predetermined amount of irregu- larities of the surface defects by a user using a Graphic User Interface (GUI) to output the defects having values not less than the threshold.

(5) Yet another aspect of the present invention is to provide a defect detecting apparatus having the method of analyzing defect data, which includes carrying out processing according to kinds of defects based on defect data obtained from an inspected surface of a disk to detect defects having features on the surface, and setting as a threshold a predetermined width or a predetermined amount of irregularities of the surface defects by a user using a Graphic User Interface (GUI) to output the defects having values not less than the threshold.

According to the present invention, a surface defect inspecting apparatus is provided, which can use a small number of detectors and circuits to detect with high accuracy the size and the height of the concave defect or the convex defect on the surface of the face plate.

These and other objects, features and advantages of the invention will be apparent from the following more particular description of preferred embodiments of the invention, as illustrated in the accompanying drawings.

BRIEF DESCRIPTION OF THE DRAWINGS

FIG. 3A is a view illustrating a deviated position of specular reflection light in a shading filter when an ascending part of a lateral inclined portion of a convex defect is scanned, and FIG. 3B is a view illustrating a deviated position of specular reflection light in the shading filter when a descending part of the lateral inclined portion of the convex defect is scanned;

FIG. 5A is a view illustrating a shading filter disposed to make the filter have a shading difference in a direction orthogonal to specular reflection light in an xz plane in an xz plane height measuring portion, and FIG. 5B is a view illustrating a shading filter disposed to make the filter have a shading difference in a direction orthogonal to specular reflection light in a yz plane in a yz plane height measuring portion;

FIG. 6A is a flow chart illustrating internal processing of an operation processing and defect determining unit, and FIG. 6B is a view illustrating a signal intensity corresponding to the flow of internal processing of the operation processing and defect determining unit;

FIG. 7A is a view illustrating a linear distribution defect, a feature on an image, and image signals, and FIG. 7B is a view illustrating a circular arc distribution defect, a feature on an image, and image signals;

FIG. 8A is a view illustrating inspection of a face plate rotating at a uniform velocity with a spirally uniform sampling pitch, and an upper portion of FIG. 8B is a view illustrating a defect position in a rectangular coordinate system and a lower portion of FIG. 8B is a view illustrating a defect position in a polar coordinate system;

FIG. 10A is a view illustrating an operator for emphasizing a horizontal line, FIG. 10B is a view illustrating an operator for emphasizing a line inclined by 45°, FIG. 10C is a view illustrating an operator for emphasizing a vertical line, and FIG. 10D is a view illustrating an operator for emphasizing a line inclined by 135°;

FIG. 11 is a view illustrating an operator for removing an isolated point;

FIG. 17A is a view illustrating input image data, FIG. 17B is a view illustrating a waveform after image data is subjected to smoothing, FIG. 17C is a view illustrating a bright level of threshold (upper line) and a dark level of threshold (lower line) with respect to a signal waveform after smoothing is carried out, and FIG. 17D is a view illustrating an image after binarization is carried out;

FIG. 20A is a view illustrating an inspection region having a segment shape set for the circular arc defect, and FIG. 20B is a view illustrating a contrast in an inspection region having a segment shape; and FIG. 21 is a view illustrating correlation between a contrast and a measured height.

DETAILED DESCRIPTION OF THE PREFERRED EMBODIMENTS

Figure 1:
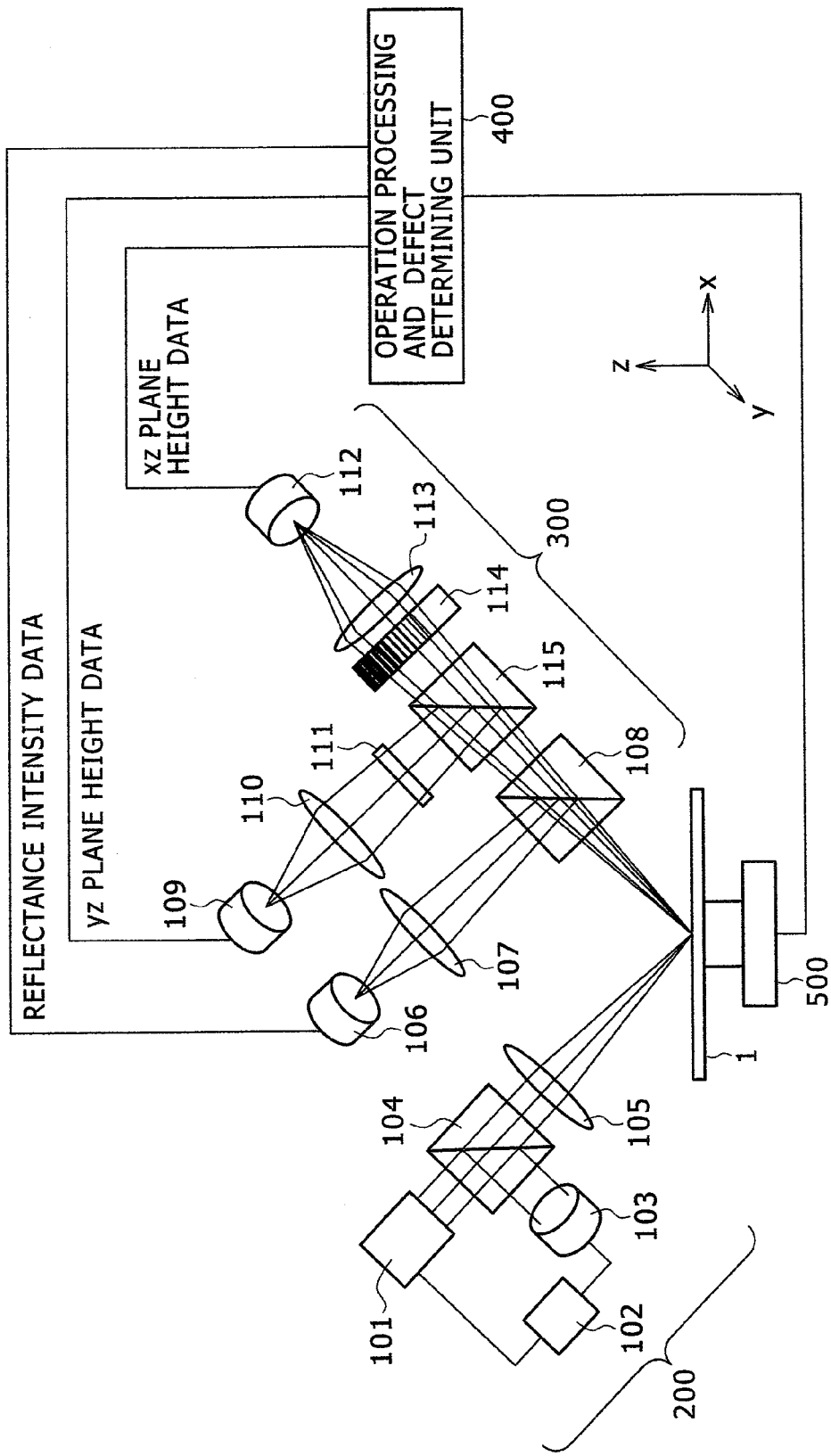
FIG. 1 is a view illustrating a schematic configuration of a surface defect inspecting apparatus associated with a first embodiment of the present invention.

FIG. 1 illustrates a surface defect inspecting apparatus having a defect detection optical system and defect-detected image processing, which includes an irradiation optical system 200 that irradiates a light beam on a surface of a face plate of a disk 1 mounted on a stage 500 to scan the surface of the face plate, a light-receiving optical system 300 having shading filters 111 and 114 with shading differences causing an amount of specular reflection light from the face plate resulting from the light beam irradiated on the disk 1 to be changed and receiving the specular reflection light that has transmitted the shading filters, and a processing unit 400 that identifies defects on the surface of the face plate from the change in amount of specular reflection light that has transmitted the shading filters. Hereinafter, details of the respective constitutional components will be described with respective operations.

In the irradiation optical system 200, a laser beam output from a laser light source 101 is divided by a beam splitter 104, and some of the divided laser beam is received by a photodiode 103, and a variation in intensity of the received laser beam is read out. A feedback control circuit 102 controls a laser power to make the laser output uniform based on the read variation in intensity.

The light beam that has transmitted the beam splitter 104 is focused by a focusing lens 105 and is incident on the face plate as a spot S. In this approach, the detection resolution depends on the size of the spot S, so that the focusing lens 105 is set to make the spot size equal to the defect size on the surface of the face plate. In addition, the focusing position is adjusted to make the focus point arranged on the surface of the face plate when focusing is performed. In addition, the main scanning direction is a θ-direction and the sub scanning direction is an r-direction, so that the disk 1 is spirally scanned on the stage 500 on the basis of r and θ by the light beam.

The light-receiving optical system 300 includes an xz plane height measuring unit, a yz plane height measuring unit, and a reflection intensity measuring unit. The specular reflection light from the inspection point S of the disk 1 is partially reflected by the beam splitter 108 in a direction of 90° with respect to an optical axis to be passed to the reflection intensity measuring unit, and half of the transmitted light is reflected by a half mirror 115 in a direction of 90° with respect to the optical axis to be passed to the yz plane height measuring unit and the rest is passed to the xz plane height measuring unit.

The xz plane height measuring unit will be first described. The specular reflection light from the inspection point S of the disk 1 transmits the filter 114 having a shading difference, is focused by the focusing lens 113, and is received by the light-receiving element 112. The shading filter 114 is a filter that has a shading difference in a direction orthogonal to the specular reflection light in the xz plane. The filter has as its performance the shading difference ranging from a transmittance of 0% to a transmittance of 100%, and is set to allow the specular reflection light of the light beam that has irradiated the position where defects are not present on the surface of the face plate to transmit the position having the transmittance of 50%, which is the central position of the filter. When the concave defect or the convex defect is present on the face plate, the region where the specular reflection light from the lateral inclined portion of the concave defect or the convex defect transmits the filter is shifted to any one of the region having a higher transmittance and the region having a lower transmittance. After the light transmits the filter, the amount of light focused by the focusing lens 113 and received by the light-receiving element 112 is changed, so that the defect can be detected from this change.

The yz plane height measuring unit will now be described. The specular reflection light reflected by 90° with respect to the half mirror 115 transmits the filter 111 having a shading difference, is focused by the focusing lens 110, and is received by the light-receiving element 109. The shading filter 111 is a filter that has a shading difference in a direction orthogonal to the specular reflection light in the yz plane. The filter has the same performance as the filter 114 such that the filter has the shading difference ranging from a transmittance of 0% to a transmittance of 100%, and is set to allow the specular reflection light of the light beam that has irradiated the position where defects are not present on the surface of the face plate to transmit the position having the transmittance of 50%, which is the central position of the filter. When the concave defect or the convex defect is present on the face plate, the region where the specular reflection light from the lateral inclined portion of the concave defect or the convex defect transmits the filter is shifted to any one of the region having a higher transmittance and the region having a lower transmittance. After the light transmits the filter, the amount of light focused by the focusing lens 110 and received by the light-receiving element 109 is changed, so that the defect can be detected from this change.

Next, the reflection intensity measuring unit will be described. The specular reflection light that is partially reflected by 90° with respect to an optical axis by the beam splitter 108 is focused by the focusing lens 107 and is received by the light-receiving element 106. The reason why the reflection intensity needs to be measured will now be described. The xz height measurement unit and the yz height measurement unit read out information of the surface irregularity as changes in light intensity. In this case, when positions having different reflectances are present on the surface of the face plate, these positions may be detected as irregular defects. Accordingly, by subtracting the amount of light used for measuring the change in specular reflectance from the value of intensity measured by the xz height measurement unit and the yz height measurement unit, it becomes possible to accurately detect the irregular defects without being affected by the change in reflectance on the surface of the face plate.

Data output from the xz plane height measuring unit, data output from the yz plane height measuring unit, and data output from the reflection intensity measurement unit is processed by the operation processing and defect determining unit 400.

Figure 2A:
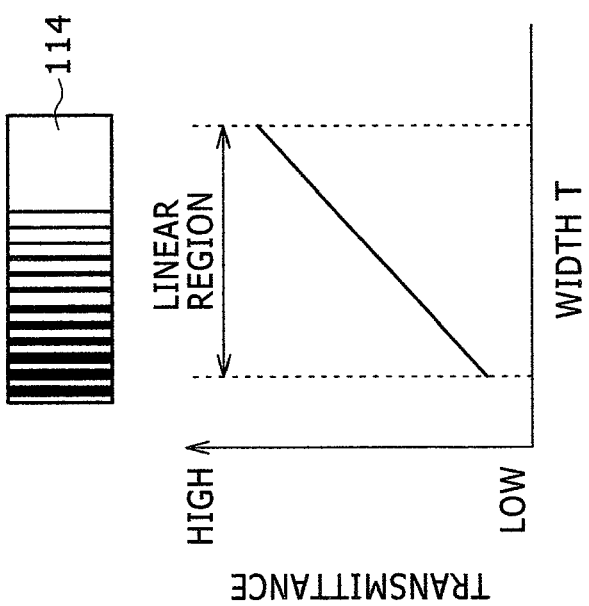
FIG. 2A is a view illustrating a transmittance characteristic of a general variable-type Neutral Density (ND) filter.
Figure 2B:
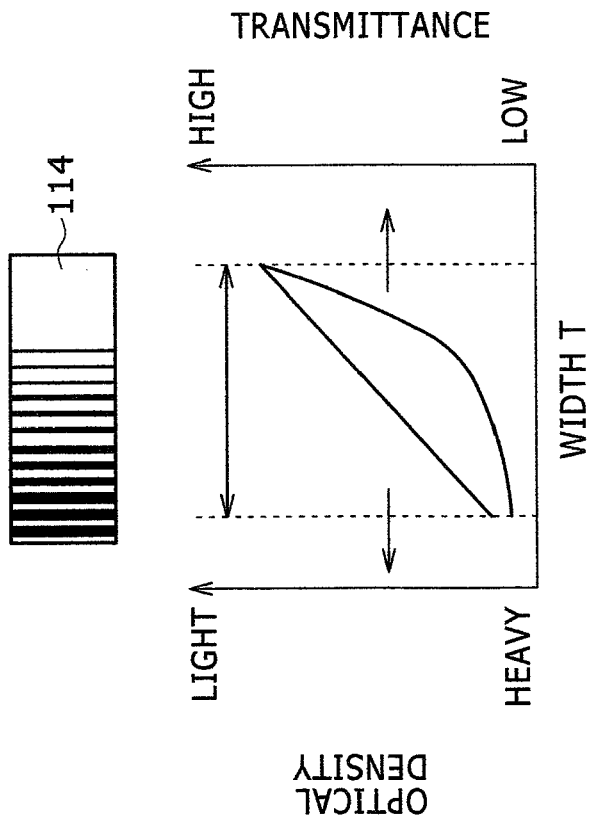
FIG. 2B is a view illustrating a transmittance characteristic of an ND filter of which an optical density is designed to make the transmittance linear with respect to the width T.

FIGS. 2A and 2B illustrate transmittance characteristics of the shading filter 114. FIG. 2A illustrates a general variable-type ND filter, which is a filter of which an optical density is linear with respect to the width T direction. When this filter is employed, the relationship between the transmittance T and the optical density D has a common logarithm below:

$$D = \log(1/T)$$

so that the transmittance is changed with respect to the width T according to the common logarithm as shown in FIG. 2A. The change in intensity that can be obtained by the surface irregularity from the equation mentioned above is changed not linearly but logarithmically, so that the processing taking this logarithmic change into consideration is required for even an intensity that can be obtained. In the meantime, FIG. 2B illustrates an ND filter of which the optical density is designed to make the transmittance linear with respect to the width T. In this case, the change in intensity that can be obtained by the surface irregularity becomes linear. A method of manufacturing the ND filter includes stepwise changing the thickness of a metal layer coated on a glass substrate so as to make the thickness yield the designed transmittance. Alternatively, a method of stepwise changing the thickness of the glass substrate so as to make the thickness yield the designed transmittance, and so on, may be employed.

FIGS. 3A and 3B illustrate that positional deviation of the specular reflection light due to the irregular defect occurs on the shading filter, wherein FIG. 3A illustrates the ascending lateral inclined portion of the convex defect being scanned. When the inclination angle of the defect is ε, the laser moves to the region having a geometrically low transmittance on the shading filter 114 away from the surface of the face plate by a distance Lε. At this time, when the shading filter has the performance allowing the change in amount of light to be read out when the laser moves by a distance Lε, it is possible to measure the inclination of the surface. In the meantime, FIG. 3B illustrates the descending lateral inclined portion of the convex defect being scanned. Unlike the case of FIG. 3A, the laser moves to a region having a geometrically high transmittance by a distance L● on the shading filter 114. At this time, when the shading filter has the performance allowing the change in amount of light to be read out when the light moves by the distance Lε, it is possible to measure the inclination of the surface.

Figure 4A:
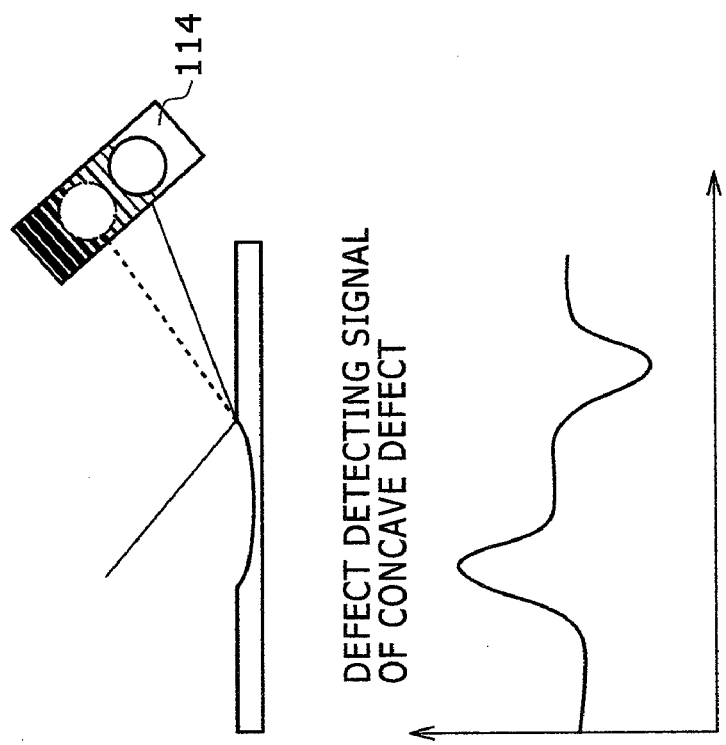
FIG. 4A is a view illustrating a waveform of a detection signal that can be obtained by detecting reflected light when a convex defect is irradiated.
Figure 4B:
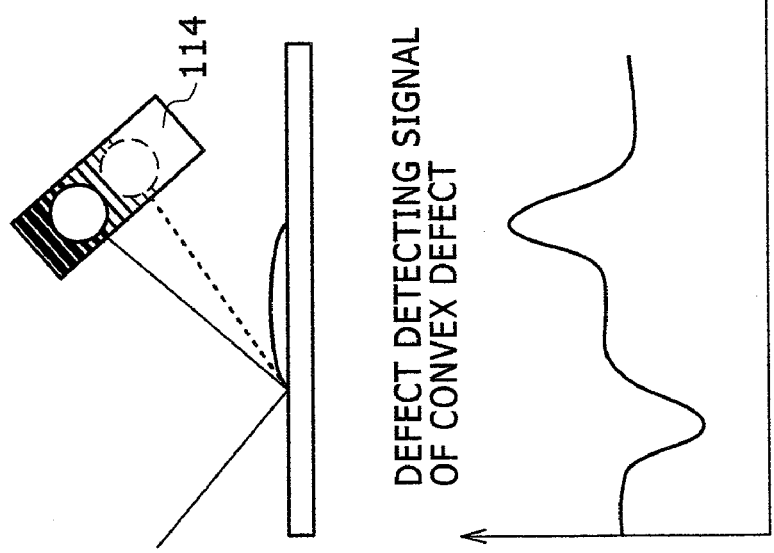
FIG. 4B is a view illustrating a waveform of a detection signal that can be obtained by detecting reflected light when a concave defect is irradiated.

FIGS. 4A and 4B illustrate a method of determining the irregular defect from the difference in detected waveform that can be obtained by the light-receiving element, wherein FIG. 4A illustrates the defect detection signal with respect to the convex defect and FIG. 4B illustrates the defect detection signal with respect to the concave defect. A pair of lateral inclined portions is present in either concave defect or convex defect, and these lateral inclined portions are substantially symmetric to each other in terms of the inclination with respect to the vertical line taken as a reference, so that the peak of the received light in right and left directions when the defect is scanned causes two shifts to be generated that are reverse each other and then return to their central position. At this time, this shift generates, as defect signals, two peaks such as positive and negative peaks. Further, lateral inclined portions of the respective recess and convex defects are inclined in the reverse direction to each other, so that the order of shifting direction is reversed in terms of right and left directions. As a result, the two peaks as the defect signals are different from each other such that the peaks first become either positive or negative in the recess and convex defects. With this configuration, the irregular defects can be determined.

FIGS. 5A and 5B illustrate the shading filter 114 in the xz plane height measuring unit and the shading filter 111 in the yz plane height measuring unit in a three-dimensional way. FIG. 5A illustrates the shading filter in the xz plane height measuring unit, which is disposed to have a shading difference in a direction orthogonal to the specular reflection light in the xz plane. In the meantime, FIG. 5B illustrates the shading filter in the yz plane height measuring unit, which is disposed to have a shading difference in a direction orthogonal to the specular reflection light in the yz plane.

FIGS. 6A and 6B illustrate an internal processing flow of the operation processing and defect determining unit 400 and signal intensities corresponding to the flow. The change in surface reflectance is reflected in xz plane height measuring data and yz plane height measuring data (step 401) which are output from the light-receiving element 112 and the light-receiving element 109, respectively. By using subtraction of data of the measured reflection intensity output by the light-receiving element 106, the effect of the change in surface reflectance can be excluded (step 402). A big waveform of the disk that can not be the defect is then removed by a high-pass filter (step 403). Analog-Digital (AD) conversion is then performed on the analog data in which the waveform is removed to convert the analog data into digital data (step 404), which is then image-processed (step 405) by the image processing unit to detect the defect (step 406).

Internal processing of the image processing unit 405 will now be described with reference to FIGS. 7 to 18 FIGS. 7A and 7B illustrate the distribution defect shapes that are to be image-processed and features on the image. FIG. 7A illustrates the linear distribution defect, which is featured to be linear on the image when the defect is detected by the optical system shown in FIG. 1. In the meantime, FIG. 7B illustrates the circular arc distribution defect, which is featured to be the circular arc on the image when the defect is detected by the optical system shown in FIG. 1. These features on the image are extracted to perform the defect detection.

FIGS. 8A and 8B illustrate the coordinate transformation of the acquired data. When the surface of the face plate is spirally inspected while being rotated with a uniform velocity at a sampling pitch as shown in FIG. 8A, the acquired data moves toward the circumference, so that a distance on the face plate per one data becomes longer. This is why the defect shape of the acquired data is different from its original shape. Accordingly, it is required to restore the original defect shape by performing the coordinate transformation from the rectangular coordinate shown in the upper part of FIG. 8B to the polar coordinate shown in the lower part of FIG. 8B.

$$x = \left(\sqrt{u^2 + v^2} - R_1\right)\left(\frac{X-1}{R_2 - R_1}\right)$$

$$y = \frac{Y}{2\pi}\tan^{-1}\left(\frac{u}{v}\right)$$

where x and y denote r and θ directional coordinates of the face plate, respectively. u and v denote the rectangular coordinate after transformation from the polar coordinate, $R_2$ denotes the outermost radius after transformation from the polar coordinate, and $R_1$, denotes the innermost radius after transformation from the polar coordinate. In this case, it is required to perform linear interpolation to make the corresponding image when x and y are decimal numbers.

Figure 9:
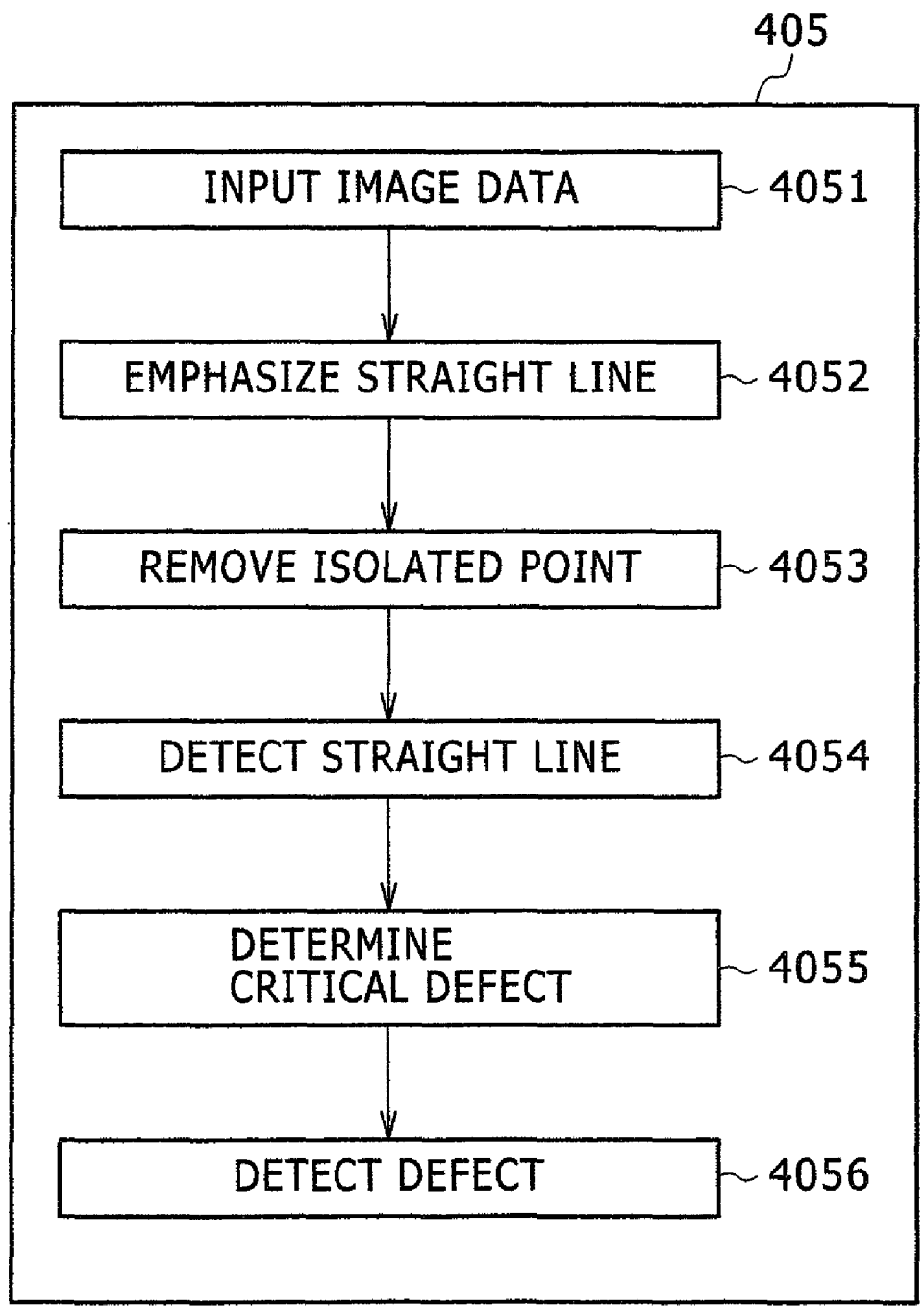
FIG. 9 is a flow chart illustrating processing of a linear defect.

FIG. 9 illustrates the image processing flow of the defect having the linear distribution feature. Image data is input (step 4051), a straight line is emphasized by enabling a straight line emphasizing operator on the data (step 4052). In this case, examples of the straight line emphasizing operator are shown in FIG. 10A to 10D. The standard size of the operator is 5×5, and this operator acts on the central pixels. The coefficient of the symbol ● is 2 and the coefficient of the symbol ● is −1, and the operator acts to extract the straight line component that has a different shading value from its neighbor. In this case, FIG. 10A illustrates the operator for emphasizing the horizontal line, FIG. 10B illustrates the operator for emphasizing the line inclined by 45°, FIG. 10C illustrates the operator for emphasizing the vertical line, and FIG. 10D illustrates the operator for emphasizing the line inclined by 135°. In addition, directivities of the straight line are not constant, so that detection operators are made to act on various directions to take the maximum evaluated value as shown below:

$$S_{max} = \text{Max}(|S^0|, |S^{45}|, |S^{90}|, |S^{135}|)$$

The reason why the absolute value is individually taken in the equation above is that both a straight line having a larger shading value than its neighbor and a straight line having a smaller shading value than its neighbor are present. After this processing, binarization is performed to make left the straight line component emphasized on the acquired data.

Next, an operator is made to emphasize connected components such as a straight line and to remove isolated components such as a noise (step 4053). In this case, an example of this operator is shown in FIG. 11. The symbol ● denotes the pixel of interest $f_{ij}$, and $W_1$ to $W_3$ denote weighted values, for example, $W_1=3$, $W_2=2$, and $W_3=1$. That is, the closer the pixel moves toward the center, the bigger weighted value is added. Although the pixel of interest is either 0 or 1, processing using the operator is not performed when the pixel is 0 but performed when the pixel is 1, thereby obtaining the emphasized evaluation value. When the pixel of interest is 1, and when the number of pixel indicating 1 on the ring (i.e., positions having the weighted value $W_1$) closest to the center is n1, the number of pixel indicating 1 on the ring (i.e., positions of the weighted value $W_2$) is n2, and the number of pixel indicating 1 on the ring (i.e., positions of the weighted value $W_3$) is n3, the evaluation value $g_{ij}$ in the pixel of interest can be obtained as shown below:

$$g_{ij} = \begin{cases} \sum_{k=1}^{m}(W_k \cdot n_k) \\ 0 \end{cases}$$

(The upper is the case when $f_{ij}=1$, and the lower is the case when $f_{ij}=0$.)

With this processing, the connected portions such as a straight line have increased evaluation values and the isolated portions such as a noise remain the same, which are subjected to binarization so that the image of which the isolated points such as the noise component are reduced can be obtained.

Figure 12A:
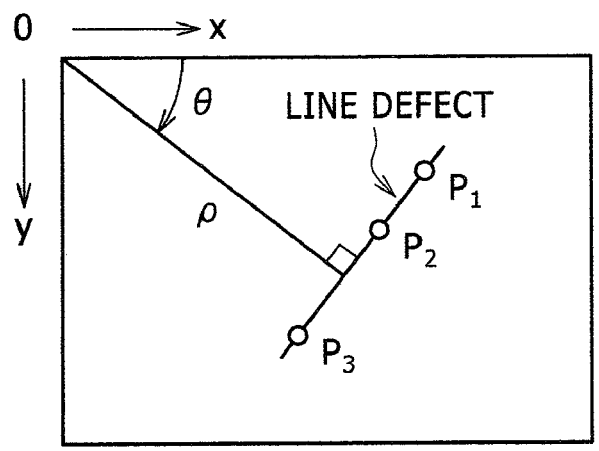
FIG. 12A is a view illustrating three point defects arranged on a straight line.
Figure 12B:
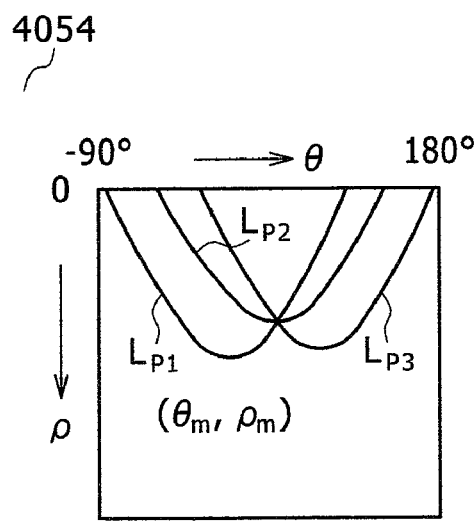
FIG. 12B is a view illustrating three defects of FIG. 12A represented in a θ-ρ space.

Next, Hough transformation is used to extract the linear component (step 4054). Referring to FIG. 12A, when three points $P_1$, $P_2$, and $P_3$ are present on the straight line, its straight line equation is as follows:

$$\rho = x \cos\theta + y \sin\theta$$

where ρ denotes a length of a perpendicular line between the upper left corner of the image and the straight line, and θ denotes an angle formed by the x-axis and the perpendicular line. At this time, one straight line is equivalent to one point on the space of θ-ρ parameters. In each point (x, y) having the value of 1 in the binarized image of interest, the set of θ-ρ meeting the equation mentioned above is calculated, which is plotted as $L_{p1}$ to $L_{p3}$ in FIG. 12B. $L_{p1}$ to $L_{p3}$ intersect only in one point, and the coordinate (θ-ρ) of the intersected point indicates the straight line constituting $P_1$ to $P_3$ shown in FIG. 12A. In other words, when the point having the biggest number of intersection (i.e., the point ($\theta_m$, $\rho_m$) having the maximum frequency) is selected on the space of θ-● parameters, the straight line determined by the point ($\theta_m$, $\rho_m$) has the most dominant component of the straight line on the binarized image.

Figure 13:
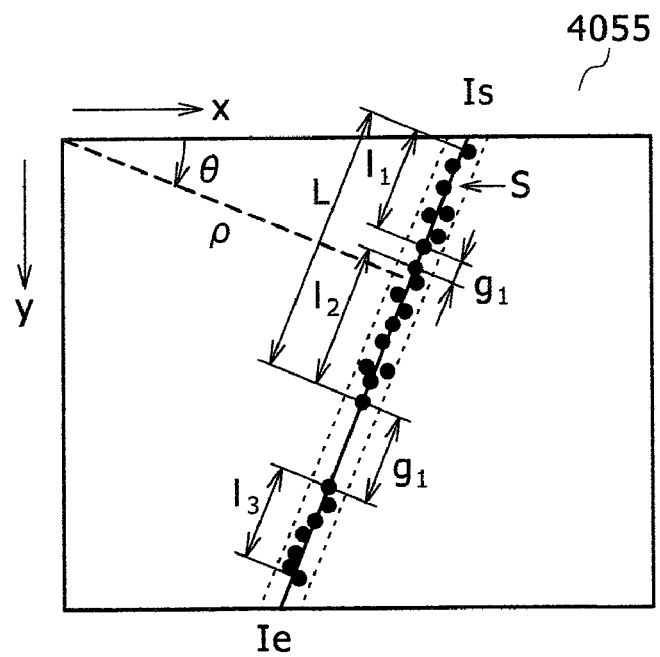
FIG. 13 is a view illustrating measured lengths with respect to the straight line detected by Hough transformation.

Next, the straight line component only is extracted from the binarized image transformed by Hough transformation, and a length of the straight line is measured (step 4055). Straight lines $I_s$ and $I_e$ are first drawn on the xy plane based on the values of ($\theta_m$, $\rho_m$) obtained in the space of θ-ρ parameters. Enlargement processing is then performed on the straight line to make the straight line thick, thereby generating a straight line defect region S. Points within this region are determined to be the constitutional components of the straight line. The reason why the straight line is made to be thick is that the line is actually not on one line but is line having a width to some extent. After this processing, lengths of segments of the line $l_1$ to $l_3$ and lengths of gaps between the segments $g_1$ and $g_2$ are measured to determine the length of the straight line. That is, when the gap is not less than a predetermined value (i.e., a threshold $g_t$), the line is not determined to be the continuously straight line. In addition, when the length of the segment is not more than a predetermined value (i.e., a threshold $l_t$), the segment is not determined to be the straight line. This is important when the noise or the very short straight line is to be removed on an actual image. Referring to FIG. 13, $g_1 < g_t$, $g_2 > g_t$, and the length of the straight line L can be obtained as follows:

$$L = l_1 + g_1 + l_2$$

Next, $L > l_t$ and $l_2 < l_t$ can be determined from the segment length determination processing, so that the straight line L is the final straight line.

Figure 14A:
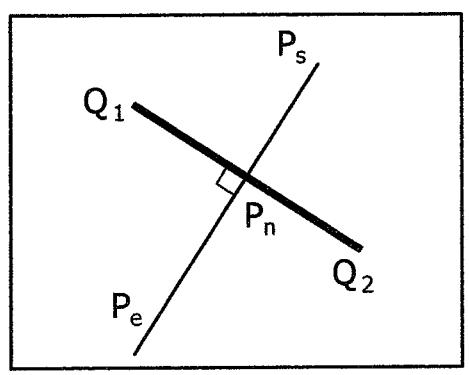
FIG. 14A is a view illustrating the relationship between a linear defect Pe-Ps and an inspection region $Q_1$-$Q_2$.
Figure 14B:
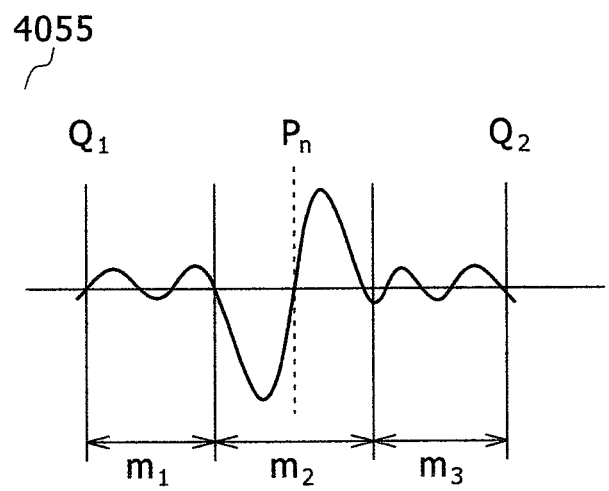
FIG. 14B is a view illustrating a contrast on the inspection region $Q_1$-$Q_2$.

In addition, since the irregularity of the disk surface causes a crash to be generated on the disk head, the height of the linear defect must also be evaluated in the critical defect determination step 4055, so that it is required to evaluate the criticality of the defect with the height determination. A method of evaluating the height using the image data is shown in FIG. 14. For example, when the surface of the face plate is inspected using the optical system shown in FIG. 1, height information is shown on the image as contrast, so that this information is used to determine the height. To detail this, as shown in FIG. 14A, the inspection region $Q_1$ to $Q_2$ orthogonal to the straight line is set to perform inspection with respect to every point of the straight line ranging from the start point $P_s$ to the end point $P_e$, and the contrast of the straight line is obtained from the density ranging from the point $Q_1$ to the point $Q_2$ in the inspection region. This will be described with reference to FIG. 14B. The inspection region $Q_1$ to $Q_2$ is divided into three regions $m_1$, $m_2$, and $m_3$, and the segment is determined to be present in the region $m_2$. The contrast is based on comparison between the central region and its neighboring regions, so that an average density of the neighboring regions is obtained by calculating contrast densities of the regions $m_1$ and $m_3$ which are outer sides of the segment. A difference between the average density value and the density value of the region $m_2$ is calculated, which is then integrated with the region $m_2$, so that the contrast can be obtained at the point $P_n$ in the segment.

$$C_n = \sum_{i \in D_2} \left| \left\{ \frac{1}{m_1 + m_3} \right\} \cdot \sum_{j \in D_1 + D_3} \{f_j\} - f_i \right| / 2$$

The value $C_n$ is calculated from the start point $P_s$ to the end point $P_e$ of the segments, which is added by accumulation and then divided by the length of the segment L, so that the average contrast $C_{av}$ is obtained.

$$C_{av} = \left( \sum_{P_s}^{P_e} C_n \right) / L$$

Figure 15:
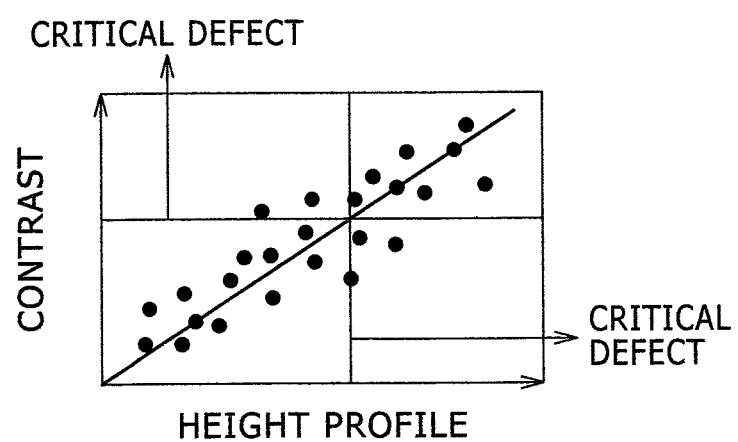
FIG. 15 is a view illustrating correlation between a defect contrast and a height of an actual profile.

The critical defect can be determined from the contrast on the linear defect detected by taking the correlation between the obtained contrast value and the height value measured from the actual profile as shown in FIG. 15.

Figure 16:
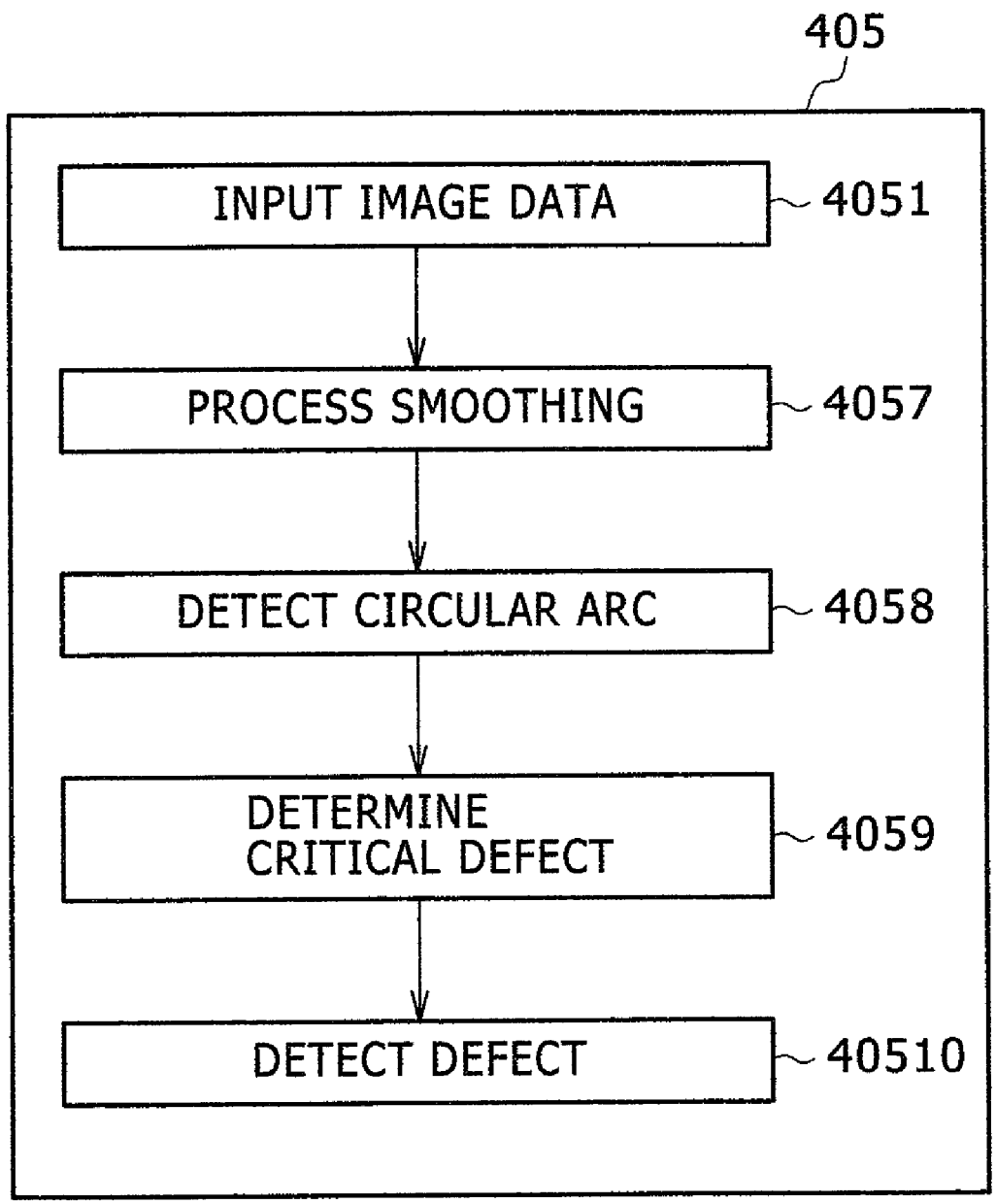
FIG. 16 is a flow chart illustrating processing of a circular arc defect.

FIG. 16 illustrates an image processing flow for the defect having a circular arc distribution feature. Image data is input (step 4051), smoothing processing is performed (using a Gaussian filter, an averaging filter, and so on) on the image data as shown in FIG. 17B to remove the noise component (step 4057). In the circular arc defect, a peak at a bright level and a peak at a dark level are present in any of the recess and convex defects, so that a threshold at the bright level and a threshold at the dark level are set with respect to the smoothed data as shown in FIGS. 17A to 17D, which are then subjected to binarization so that the circular arc distribution is formed on the image. The smoothing processing is performed on the input image data as shown in FIG. 17A to obtain the signal waveform as shown in FIG. 17B, and the threshold at the bright level (i.e., the upper line) and the threshold at the dark level (i.e., the lower line) are set with respect to the signal waveform as shown in FIG. 17C, which are then subjected to binarization to obtain the image as shown in FIG. 17D.

Figure 18A:
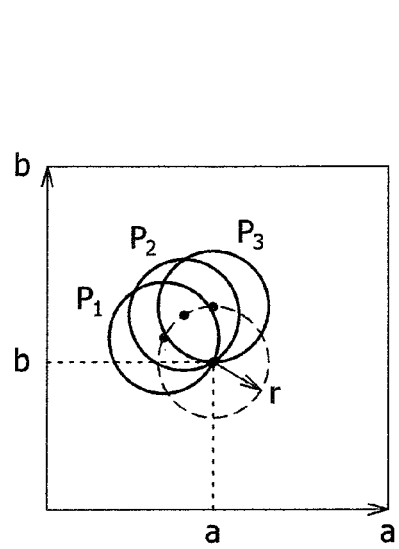
FIG. 18A is a view illustrating three points $P_1$, $P_2$, and $P_3$ present on an arc of the same circle having a radius of r.

Hough transformation is used to extract the circular arc component (step 4058). Referring to FIG. 18A, for example, when three points $P_1$, $P_2$, and $P_3$ are present on the same circle having a radius r, the circular equation is as follows:

$$(x-a)^2 + (y-b)^2 = r^2$$

where the symbols a and b denote the center coordinate of the circle. A method of calculating the center coordinate (a, b) includes drawing circles having the points $P_1$, $P_2$, and $P_3$ as respective centers and determining the circle with the most intersection number of the drawn circles. When this processing is applied to the pixels having the value 1 over the entire image, candidates of the center coordinates of the circle can be obtained.

Figure 18B:
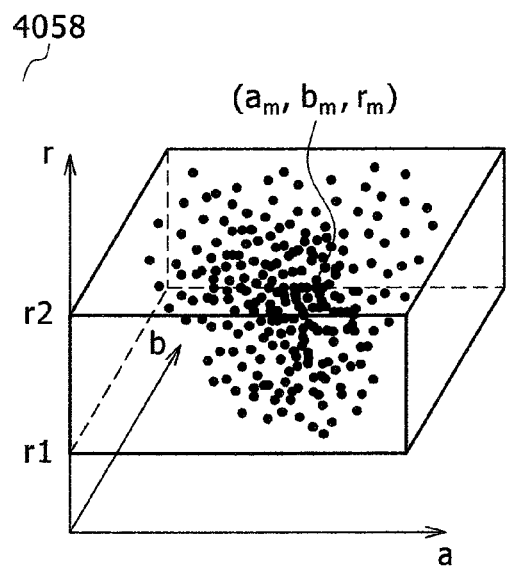
FIG. 18B is a view illustrating information of the arc plotted in a space formed by the central coordinate (a, b) of the arc and the radius.

The radius of the circular arc defect that may be determined to be a defect is arbitrary, so that the defect having the radius ranging from $r_1$ to $r_2$ are determined to be the critical defect. In this case, selection of the points having a large amount of intersections is performed on the space $(a_m, b_m, r_m)$ as shown in FIG. 18B, and the radii and center coordinates of the circular arc defects are obtained from the selected points.

Figure 19:
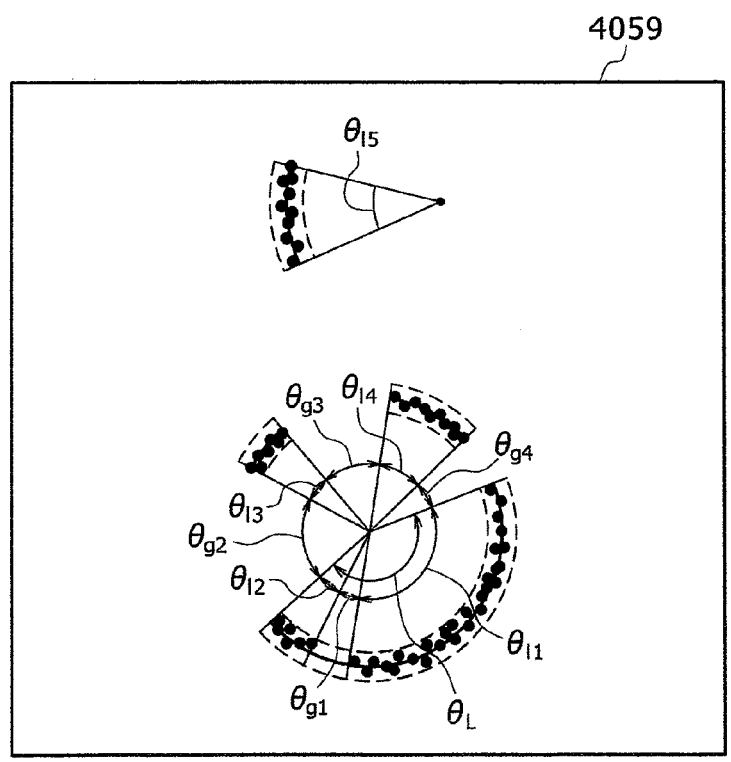
FIG. 19 is a view illustrating measured lengths with respect to the arc detected by Hough transformation.

Next, the circular arc component only is extracted from the binarized image transformed by Hough transformation, and a length of the circular arc is measured (step 4059). A circle is first drawn on the xy plane based on the values of $(a_m, b_m, r_m)$ obtained in the space of a, b, and r parameters. Enlargement processing is then performed thereon to make the line thick, thereby generating a circular arc defect region S. Points within this region are determined to be the constitutional components of the circular arc. The reason why the line is made to be thick is that a circular arc defect is actually not on one line but is the circular arc defect having a width to some extent. After this processing, lengths of segments $r\theta_{l1}$ to $r\theta_{l4}$ and gaps between the segments $r\theta_{g1}$ to $r\theta_{g4}$ are measured to determine the length of the circular arc. That is, when the gap is not less than a predetermined value (i.e., a threshold $r\theta_{gt}$), the circular arc is not determined to be the continuous circular arc. In addition, when the length of the segment is not more than a predetermined value (i.e., a threshold $r\theta_{lt}$), the segment is not determined to be the straight line. This is important when the noise or the very short straight line is to be removed on an actual image. Referring to FIG. 19, $r\theta_{g1} < r\theta_{gt}$, $r\theta_{g2} > r\theta_{gt}$, $r\theta_{g3} > r\theta_{gt}$, $r\theta_{g4} > r\theta_{gt}$, and the length of the circular arc $r\theta_L$ can be obtained as follows:

$$r\theta_L = r\theta_{l1} + r\theta_{g1} + r\theta_{l2}$$

Next, $r\theta_L > r\theta_{lt}$, $r\theta_{l4} > r\theta_{lt}$, $r\theta_{l5} > r\theta_{lt}$, and $r\theta_{l3} < r\theta_{lt}$ can be determined from the segment length determination processing, so that the circular arc $r\theta_L$, $r\theta_{l4}$, and $r\theta_{l5}$ is the final circular arc.

It is determined whether the additionally obtained circular arc is the defect on the circular arc. According to this decision, for example, $r\theta_L$ and $r\theta_{l4}$ have the same center coordinate in FIG. 19 so that they are determined to be one circular arc, and $r\theta_{l5}$ has a different center coordinate so that it is determined to a different circular arc. In this case, it is determined whether the different circular arc is the defect on the circular arc using a rate of $\theta_L$ and $\theta_{l4}$ occupied in the circumference $2\pi$. When $r\theta_{l5}$ has a low rate in the circumference, it is determined not to be the defect on the circular arc.

In addition, since the irregularity of the disk surface causes a crash to be generated on the disk head, the height of the circular arc defect must also be evaluated in the critical defect determination step 4059, so that it is required to evaluate the criticality of the defect with the height determination. A method of evaluating the height using the image data is shown in FIGS. 20A and 20B. For example, when the surface of the face plate is inspected using the optical system shown in FIG. 1, height information is shown on the image as contrast, so that this information is used to determine the height. To detail this, as shown in FIG. 20A, the inspection region $Q_1$ to $Q_2$ is set to perform inspection with respect to every point on the circular arc ranging from 0° to 180°, and the contrast of the straight line is obtained from the density ranging from the point $Q_1$, to the point $Q_2$ in the inspection region. This will be described with reference to FIG. 20B. The inspection region $Q_1$ to $Q_2$ is divided into three regions $m_1$, $m_2$, and $m_3$, and the segment is determined to be present in the region $m_2$. The contrast is based on comparison between the central region and its neighboring regions, so that an average density of the neighboring regions is obtained by calculating contrast densities of the regions $m_1$ and $m_3$ which are outer sides of the segment. A difference between the average density value and the density value of the region $m_2$ is calculated, which is then integrated with the region $m_2$, so that the contrast can be obtained at the point $P_n$ in the segment.

$$C_n = \sum_{i \in D_2} \left| \left\{ \frac{1}{m_1 + m_3} \right\} \cdot \sum_{j \in D_1 + D_3} \{f_j\} - f_i \right| / 2$$

The value $C_n$ is calculated from 0° to 180° of the circular arc, which is added by accumulation and then divided by the length of the segment L, so that the average contrast $C_{av}$ is obtained.

$$C_{av} = \left( \sum_{0}^{180} C_\theta \right) / N$$

The critical defect can be determined from the contrast on the linear defect detected by taking the correlation between the obtained contrast value and the height value measured from the actual profile as shown in FIG. 21.

Although the present invention has been described in detail with respect to preferred embodiments, it goes without saying that the present invention is not limited to the preferred embodiments mentioned above and may be variously modified without departing from the spirit of the present invention.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A defect inspecting apparatus comprising:
    an irradiating optical system for irradiating a light beam on a surface of a disk;
    a first light-receiving optical system having a first sensor which receives a specular reflection light reflected from the disk by the irradiation of the light beam and passed through a first filter having a shading difference; and
    a signal processing unit for detecting defects on the disk based on an amount of light obtained by the first light-receiving optical system through the first filter.

2. The defect inspecting apparatus according to claim 1, wherein the first filter is a filter of which an optical density changes linearly.

3. The defect inspecting apparatus according to claim 1, further comprising:
    a second light-receiving optical system having a second sensor which receives the specular reflection light reflected from the disk by the irradiation of the light beam and passed through a second filter,
    wherein the first filter is a filter having a shading difference in a direction substantially orthogonal to the specular reflection light in an xz plane, and the second filter is a filter having a shading difference in a direction substantially orthogonal to the specular reflection light in a yz plane.

4. The defect inspecting apparatus according to claim 3, wherein the second filter is a filter of which an optical density changes linearly.

5. The defect inspecting apparatus according to claim 3, further comprising:
    a third light-receiving optical system having a third sensor which receives the specular reflection light reflected from the disk by the irradiation of the light beam,
    wherein the signal processing unit detects defects on the disk using information of an amount of light obtained by the first light-receiving optical system, information of an amount of light obtained by the second light-receiving optical system, and information of an amount of light obtained by the third light-receiving optical system.

6. A defect inspecting apparatus comprising:
    an irradiating optical system for obliquely irradiating a light beam on a surface of a disk;
    a light-receiving optical system having a sensor which receives a specular reflection light reflected from the disk by the oblique irradiation of the light beam and passed through a filter; and
    a signal processing unit for detecting defects on the disk based on a signal output from the sensor,
    wherein the signal processing unit forms an image of a defect by processing the signal output from the sensor and processes the image to extract a feature of a distribution defect shape of the image by applying a process flow unique to the distribution defect shape of the image.

7. The defect inspecting apparatus according to claim 6, wherein when the surface of the disk corresponds to an xy plane and a direction vertical to the xy plane corresponds to a z direction, the light-receiving optical system includes an xz plane height measuring unit of measuring the xz plane height, a yz plane height measuring unit of measuring the yz plane height, a specular reflection light intensity measuring unit of measuring the intensity of the specular reflection light, and a branch unit of branching the specular reflection light reflected from the disk, and branches the specular reflection light reflected from the disk in the branch unit to detect the branched light in each of the xz plane height measuring unit, the yz plane height measuring unit, and the specular reflection light intensity measuring unit, and the signal processing unit detects the defects on the disk using signals obtained by the xz plane height measuring unit, the yz plane height measuring unit, and the specular reflection light intensity measuring unit of the light-receiving optical signal that have detected the reflection light reflected from the disk.

8. The defect inspecting apparatus according to claim 7, wherein the xz plane height measuring unit of the light-receiving optical system has a first filter of which an optical density is changed according to a region of the first filter, and the yz plane height measuring unit has a second filter of which an optical density is changed according to a region of the second filter.

9. The defect inspecting apparatus according to claim 6, wherein the signal processing unit detects defects including a linear defect and a circular arc defect as the extracted defects.

10. The defect inspecting apparatus according to claim 6, further comprising:
- an input unit that inputs the threshold; and
- a storage unit that stores the threshold input by the input unit.

11. A method of inspecting defects, comprising:
- obliquely irradiating a light beam on a surface of a disk;
- receiving a specular reflection light reflected from the disk by the oblique irradiation of the light beam and passed through a filter; and
- detecting defects on the disk based on a signal obtained by receiving the specular reflection light reflected from the disk,
- wherein the detecting of the defects forms an image of a defect by processing the signal output from the sensor and processes the image to extract a feature of a distribution defect shape of the image by applying a process flow unique to the distribution defect shape of the image.

12. The method according to claim 11, wherein when the surface of the disk corresponds to an xy plane and a direction vertical to the xy plane corresponds to a z direction, the receiving of the specular reflection light from reflected the disk includes branching the reflection light from the disk to detect light containing height information within the xz plane, light containing height information within the yz plane, and an intensity of the specular reflection light, and the detecting of the defects includes detecting the defects on the disk using the light containing the height information within the xz plane, the light containing the height information within the yz plane, and a signal obtained by the detected intensity of the reflection light.

13. The method according to claim 12, wherein the receiving of the specular reflection light from the disk includes detecting the light containing the height information within the xz plane by detecting the specular reflection light that has transmitted a first filter of which an optical density is changed according to a region of the first filter, and detecting the light containing the height information within the yz plane by detecting the specular reflection light that has transmitted a second filter of which an optical density is changed according to a region of the second filter.

14. The method according to claim 11, wherein the detecting of the defects includes detecting a linear defect and a circular arc defect as the extracted defects.

15. The method according to claim 11, wherein the threshold is input from a graphic user interface (GUI).

\* \* \* \* \*